US009702873B2

United States Patent
Gordon et al.

(10) Patent No.: US 9,702,873 B2
(45) Date of Patent: Jul. 11, 2017

(54) SYSTEM FOR TRAPPING, INTERACTING AND MODIFYING SINGLE PROTEIN MOLECULES USING A DOUBLE-NANOHOLE STRUCTURE

(71) Applicant: UVic Industry Partnerships Inc., Victoria (CA)

(72) Inventors: Reuven Gordon, Victoria (CA); Yuanjie Pang, Ann Arbor, MI (US)

(*) Notice: Subject to any disclaimer, the term of this patent is extended or adjusted under 35 U.S.C. 154(b) by 597 days.

(21) Appl. No.: 13/964,990

(22) Filed: Aug. 12, 2013

(65) Prior Publication Data
US 2014/0045277 A1    Feb. 13, 2014

Related U.S. Application Data

(60) Provisional application No. 61/682,642, filed on Aug. 13, 2012.

(51) Int. Cl.
| | | |
|---|---|---|
| *G01N 21/01* | (2006.01) | |
| *G01N 33/566* | (2006.01) | |
| *G01N 21/35* | (2014.01) | |
| *G01N 21/64* | (2006.01) | |
| *G01N 21/65* | (2006.01) | |

(52) U.S. Cl.
CPC ........... *G01N 33/566* (2013.01); *G01N 21/35* (2013.01); *G01N 21/64* (2013.01); *G01N 21/65* (2013.01)

(58) Field of Classification Search
CPC ........ G01N 21/35; G01N 21/64; G01N 21/65; G01N 33/566; G01N 33/48721; G01N 21/554; G01N 27/3278; B82Y 15/00; B82Y 20/00
See application file for complete search history.

(56) References Cited

U.S. PATENT DOCUMENTS

| 5,620,857 A   * | 4/1997  | Weetall et al. ............... 435/7.1 |
|---|---|---|
| 6,897,950 B2 * | 5/2005  | Li et al. ....................... 356/301 |
| 2006/0275541 A1* | 12/2006 | Weimer ...................... 427/96.1 |
| 2007/0183934 A1* | 8/2007  | Diercks et al. ............... 422/100 |

OTHER PUBLICATIONS

Heng et al., An optical tweezer actuated, nanoaperture-grid based optofluidic microscope implementation, 2007, Optics Express, vol. 15, No. 25, pp. 16367-16375.*
Chen et al., Enhanced optical trapping and arrangement of nano-objects in a plasmonic nanocavity, 2012, Nano Letters, vol. 12, pp. 125-132.*

(Continued)

*Primary Examiner* — Erik B Crawford
(74) *Attorney, Agent, or Firm* — Klarquist Sparkman, LLP

(57) ABSTRACT

Molecules or particle having a hydrodynamic radius as small as 3.5 nm can be trapped using a double-nanohole structure defined in a metal film or other metallic layer. Application of a suitable optical radiation flux to the double-nanohole structure can provide a folding and/or binding of protein molecules that can be identified based on changes in optical transmission. Varying nanohole transmissions can thus be associated with trapping, binding and unfolding of biological particles. The double-nanohole defines cusps, but such cusps can be defined in other ways as well.

30 Claims, 12 Drawing Sheets

(56) References Cited

OTHER PUBLICATIONS

Zhang et al., Trapping and sensing 10 nm metal nanoparticles using plasmonic dipole antennas, 2010, Nano Letters, vol. 10, pp. 1006-1011.*

Pang, Y.; Gordon, R. "Optical Trapping of 12 nm Dielectric Spheres Using Double-Nanoholes in a Gold Film," *Nano Lett*. 2011, 11(9): pp. 3763-3767 (Aug. 2011).

Zehtabi-Oskuie A.; Bergeron, J. G.; Gordon, R. "Flow-dependent double-nanohole optical trapping of 20 nm polystyrene nanospheres," *Scientific Reports* 2(966): pp. 1-4 (Dec. 2012).

Zehtabi-Oskuie, A.; Jiang, H.; Cyr, B.; Rennehan, D.; Al-Balushi, A.; Gordon, R. "Double nanohole optical trapping: Dynamics and protein-antibody co-trapping," *Lab Chip* 13: pp. 2563-2568 (Feb. 2013).

\* cited by examiner

FIGS.
5A-5F

SYSTEM FOR TRAPPING, INTERACTING AND MODIFYING SINGLE PROTEIN MOLECULES USING A DOUBLE-NANOHOLE STRUCTURE

CROSS REFERENCE TO RELATED APPLICATION

This application claims the benefit of U.S. Provisional Application 61/682,642, filed Aug. 13, 2012, which is incorporated herein by reference.

FIELD

The disclosure pertains to trapping and/or sensing and/or interacting biological particles, for example, single virus particles (virions), single protein molecules, or nanoparticles.

BACKGROUND

The prior art discloses that trapping techniques can gently immobilize and manipulate small objects, which is useful in many applications. In particular, optical trapping, which uses the momentum change of light scattering to impart forces on small objects, has been applied to trap dielectric nanospheres, carbon nanotubes, semiconductor nanowires, and metal nanoparticles. Optical trapping has great potential in microbiology applications because of its ability to trap tiny bio-particles without inducing damage. Direct optical trapping of biological particles, however, has been limited to relatively large objects, for example, living cells, bacteria, 300 nm long tobacco mosaic virus particles and DNA strains. For smaller particles, a common approach is to tether the end of the particle onto a large micrometer-sized bead. This introduces steric hindrance, hydrodynamic effects and experimental complexity (e.g. the need for binding).

Direct trapping and manipulation of smaller biological and other particles such as nanoparticles, quantum dots, and colloidal particles remains challenging, primarily because the difficulty of trapping a nonresonant dielectric particle dramatically increases as the particle size decreases. For example, using a traditional perturbative trap, the laser power needed to trap a particle, for a given average time, scales with the inverse fourth power of the particle. Due to the above mentioned disadvantages it is desired to directly manipulate nanoparticles with optical forces without tethering, and improved methods and apparatus are needed.

SUMMARY

Methods and apparatus that permit single particle trapping are disclosed using a double-hole setup. Such trapping can unfold proteins and serves to provide a highly sensitive sensor.

According to some examples, sensors comprise an optical trap and an optical system configured to provide an indication of a trapping by the optical trap based on optical power received from the optical trap. In representative examples, the optical trap comprises a double nanohole assembly, and the optical system includes an optical radiation source configured to irradiate the nanohole assembly. In other embodiments, an optical radiation detector is configured to provide the indication of trapping based on changes in detected optical power. In typical examples, the double nanohole assembly defines a first conductive tip and a second conductive tip having a tip separation of less than about 10, 15, 20, 25, 40, 50, 100 or 500 nm. In other examples, the optical system includes a waveplate configured to provide a state of polarization of the optical radiation from the optical radiation source that is aligned with a gap between the first and second conductive tips. In further embodiments, the double nanohole assembly includes two nanoholes defined in a plasmonic layer, and the tips are defined by the nanoholes in the plasmonic layer. In some examples, the plasmonic layer is a metallic layer.

Methods comprise receiving a specimen at a double nanohole assembly and based on optical radiation transmitted by the double nanohole assembly, identifying a trapping state. In some examples, at least two trapping states are identified based on the transmitted optical radiation. In other examples, methods comprise applying a sample to a plasmonic tip pair having a predetermined tip gap. The sample and the plasmonic tip pair are exposed to optical radiation polarized parallel to an axis extending between the tip pair so as to trap at least a portion of the sample.

The foregoing and other objects, features, and advantages of the invention will become more apparent from the following detailed description, which proceeds with reference to the accompanying figures.

BRIEF DESCRIPTION OF THE DRAWINGS

As shown in FIG. 8, the trapped molecule is released at about 925 sec. at a flow rate of about 12 μl/min.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In describing representative embodiments, selected implementation features are used for convenient description. However, other approaches can be used, and the disclosed examples are not to be taken as limiting the scope of the disclosure. As used herein, optical radiation refers to electromagnetic radiation in a wavelength range of from about 100 nm to about 2000 nm, but other wavelengths of electromagnetic radiation can be used as desired.

Figures 1A, 1B, 1C:
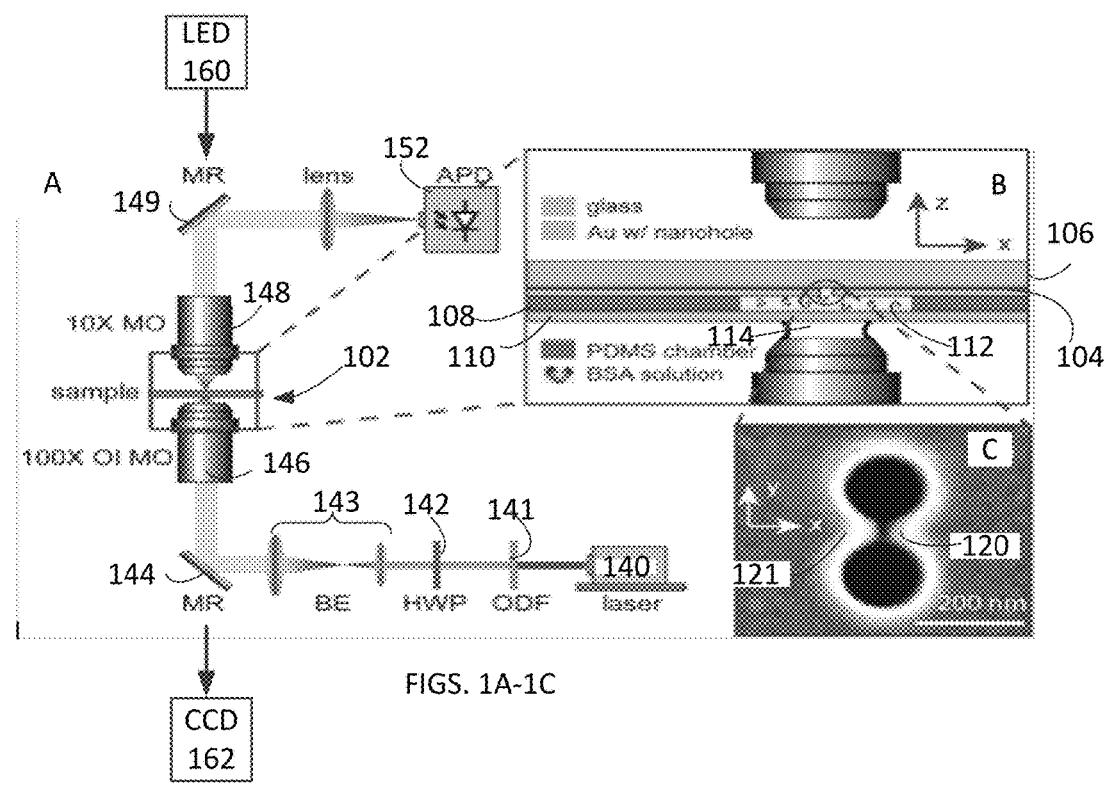
FIG. 1A is a schematic diagram of a representative assembly for optical trapping. Abbreviations used: ODF=optical density filter; HWP=half-wave plate; BE=beam expander; MR=mirror; MO=microscope objective; OI MO=oil immersion microscope objective; APD=avalanche photodiode.
FIG. 1B is an enlargement of a portion of FIG. 1(a) showing details of the sample, the microfluidic chamber, and the setup of an oil immersion microscope objective and a condenser microscope objective.
FIG. 1C is an SEM image of a representative double-nanohole.

FIGS. 1(a)-1(b) show a schematic of a representative arrangement. A double-nanohole assembly 102 was formed by milling double nanoholes on a commercially available Au film 104 on a glass substrate 106 using a focused ion beam. In other examples, other suitable metals or other conductors and other methods of creating nanoholes within the conductors can be used. Au is a plasmonic metal that permits the coupling of light into a gap plasmon mode between the two tips generating a highly enhanced local field for the trapping point. A specimen volume 112 is defined by the gold layer 106 on the glass substrate 106, a poly(dimethylsiloxane) (PDMS) layer 108, and a cover slip 110. An index matching fluid or a microscope objective immersion fluid 114 is also typically provided for operation at large numerical apertures. FIG. 1(c) shows a scanning electron microscope (SEM) image of the double-nanohole assembly 102 with two sharp tips (cusps) 120, 121. Tip separation used in this example was 15 nm, but other tip separations can be used.

In a double-nanohole optical trap, trapping is generally superior when the tip separation is barely or slightly larger than a particle to be trapped. See, for example, Pang and Gordon, "Optical Trapping of 12 nm Dielectric Spheres Using Double-Nanoholes in a Gold Film," *Nano Lett.* 2011 11, 3763-3767 (2011) which is incorporated herein by reference. In the examples described herein, bovine serum albumin (BSA) is used. Since a BSA particle has dimensions of about 14×4×4 $nm^3$, a 15 nm tip separation is chosen. A plurality of double-nanoholes can be defined on a single substrate as, for example, a regular array. The separation between each double-nanohole can be selected to be larger than the diffraction limited laser spot size so that only one of the double nanoholes can be illuminated at one time about. For example, a 20 μm separation can be selected that is larger than a representative diffraction limited laser spot size (1.1 μm).

Bovine serum albumin (BSA) solution in phosphate buffered saline (PBS) buffer is used as an example, although other suitable substances can be used. The BSA/PBS solution was sealed at the Au surface using a microwell consisting of a poly(dimethylsiloxane) spacer and a glass microscope coverslip as shown in FIG. 1(b). An optical source 140 such as an 820 nm wavelength laser (Sacher Lasertechnik Group, Model TEC 120) is configured to direct an optical radiation flux through an attenuator 141, a half wave retarder 142, and a beam expander 143. The beam expander 143 is generally configured to expand the laser beam so as to fill an aperture of a focusing objective 146 so as to produce a suitable small diameter focused spot. At least a portion of the optical radiation exiting the nanohole assembly is directed by a microscope objective 148 to a photodetector 152, such as a silicon avalanche photodetector. The photodetector 152 is coupled to detection/amplifier circuits and bias circuits but these electronics are not shown in FIGS. 1(a)-1(c). The focusing objective is typically a high numerical aperture (>1) microscope objective, and a silicon APD is well suited for detection of an 820 nm laser beam, but other detectors might be preferred at other wavelengths. Trapping is wavelength dependent as well, and 820 nm optical radiation or radiation at other wavelengths can be used. In addition, the 820 nm wavelength also has a lower absorption in water but other suitable wavelengths can be selected based on an absorption spectrum in the specimen used.

In an example, the laser beam was focused onto the sample using a 100× oil immersion microscope objective (1.25 numerical aperture) in a state of polarization such that the electric field aligned with the tips of the double-hole (i.e., along the x-direction in FIG. 1(c)). Typically, the laser 140 provides a polarized optical beam, and the half wave retarder can be rotated to align the beam electric field. Transmitted light through the double-nanohole was collected using a 10×-condenser microscope objective (0.25 numerical aperture) and measured with a silicon-based avalanche photodiode (APD) (Thorlabs APD110A). A data acquisition board was used to record the voltage values generated by the APD at a sampling frequency of 2 kHz, but is not shown in the drawings. Higher sampling rates can be used and may be desirable in measurements of fast events such as protein folding or molecular binding.

The 820 nm laser beam is focused into and collimated by a fiber coupling port (Thorlabs PAF-7-X-B), but this can be omitted if the laser beam is already collimated. The collimated laser beam is then expanded using a beam expander such as a beam expander consisting of two convex lenses with different focal lengths, or other beam expander. Beam expanding is used in order to fill the whole numerical aperture of the oil immersion microscope objective. The laser beam is then reflected with a shortpass dichroic mirror 144, for example, a Thorlabs reflector (DMSP805, 50% Trans./Refl. at 805 nm). A 100× oil immersion microscope objective having a numerical aperture NA=1.25 focuses the trapping optical beam to the sample, and a 10×-condenser microscope objective (0.25 numerical aperture) collects transmitted radiation. The laser beam after the condenser objective is reflected by another dichroic mirror 149 (similar to or identical to the mirror 144) into the APD. An APD is convenient in that it provides the required sensitivity, and is more robust than a photomultiplier tube. An imaging light source 160 such as a light emitting diode (LED) can be situated to direct an illumination beam through the mirror 149 and the lens 148. Typically, the illumination beam is at a wavelength short enough to be transmitted by the shortpass mirrors 144, 149. The illumination beam is focused onto the sample and transmitted portions of the illumination beam are directed to the lens 146 and through the reflector 144 so that an image of the sample area can be obtained with a camera such as a CCD camera 162.

Figure 5:
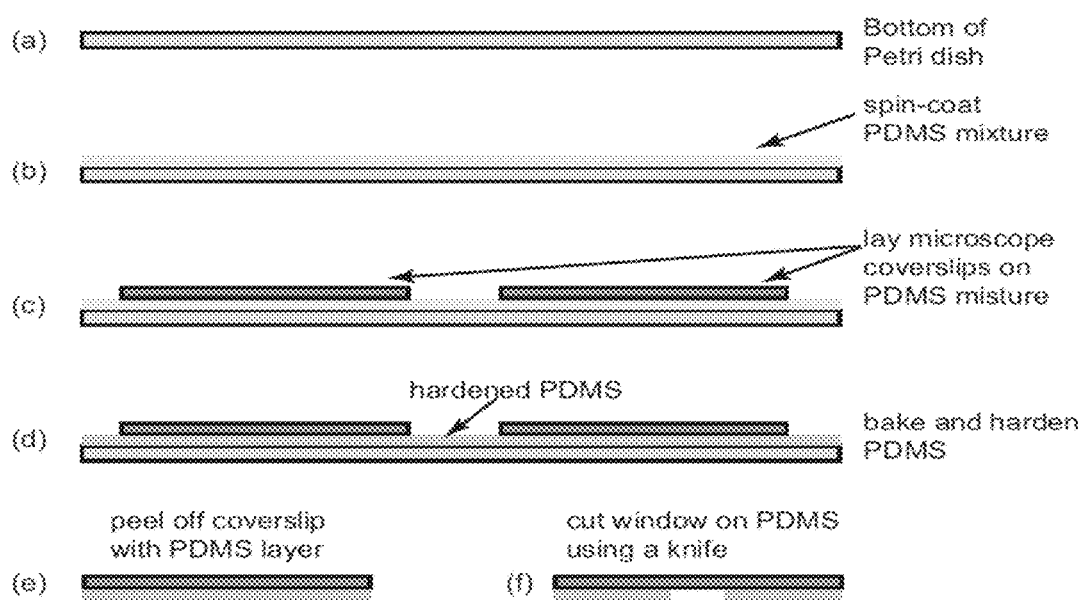
FIGS. 5A-5F illustrate a process flow diagram illustrating the fabrication of a microfluidic channel consisting of a microscope coverslip and a PDMS spacer well.
Figure 6:
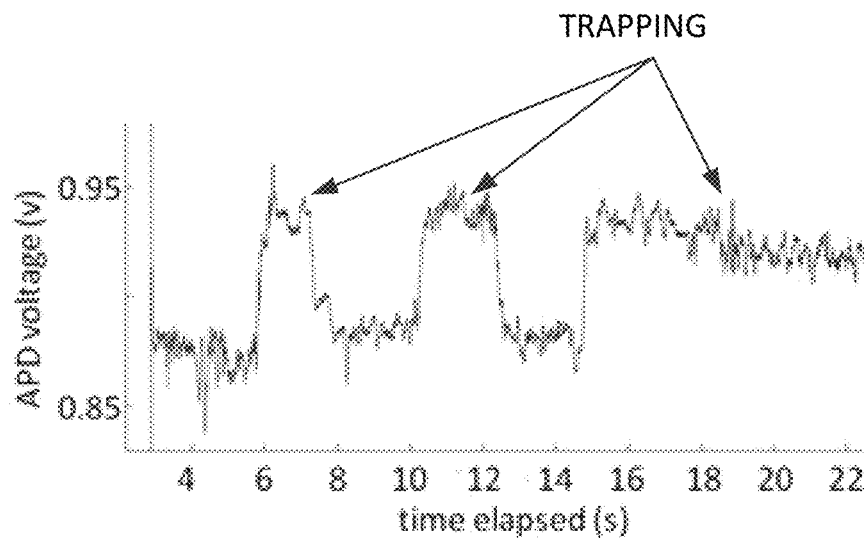
FIG. 6 includes a graph of transmitted optical power through the double-nanohole a function of time, showing trapping of ~10 nm core-shell CdS quantum dots.

The BSA solution is sealed at the Au film sample using a microfluidic channel which consists of a microscope coverslip and a PDMS spacer well. The fabrication steps of the channel are described below. PDMS base (Sylgard 184 Silicone Elastomer Base, Dow Corning Canada) was mixed with Sylgard 184 Silicone Elastomer Curing Agent (Dow Corning Canada) at a ratio of 10:1. The mixture was then degasified in a vacuum chamber for 30 minutes. As FIGS. 5(a)-5(b) show, the PDMS mixture was spin-coated onto the bottom of a Petri dish using a spin-coater (Specialty Coating System G3P-8 Spin-Coat System) at a spin rate of 950 RPM for 10 s for spreading, and then at a spin rate of 950 RPM for 60 s. The glass coverslip was then placed on top of the spin-coated PDMS mixture (FIG. 5(c)). Due to the high viscosity of the PDMS mixture, the glass coverslip remains on top of the mixture. The coverslip-covered PDMS mixture was then degasified again in a vacuum chamber for 30 minutes to remove any air bubbles between the coverslip and the PDMS mixture, i.e. to make a seamless contact between the coverslip and the PDMS. The coverslip-covered PDMS mixture was then cured using a hot plate for 10 minutes to harden the PDMS (FIG. 5(d)). After the curing, the coverslip could be peeled from the bottom of the Petri dish with the PDMS layer on the coverslip (FIG. 5(e)), since PDMS is more adhesive to glass than to the Petri dish (made of PMMA). A window of about 3 mm by 3 mm in size was then cut and removed from the PDMS as the microfluidic channel (FIG. 5(f)). The thickness of the coverslip and the PDMS spacer well is selected so that the working distance of the oil immersion microscope objective can reach the Au film. The final thickness of the PDMS spacer layer can be measured by a micrometer gauge. It is found that an error of about 10 μm is usually associated with the thickness. This error is possibly due to the unevenness of the PDMS layer induced in the 30-minute vacuuming after the spin-coating. Any slight tilt of the Petri dish will make the PDMS mixture uneven. Nevertheless, the 10 μm error in the PDMS spacer layer thickness is not a critical issue in trapping. As long as the PDMS spacer layer is thinner than 80 μm, the entire microfluidic chamber is within the working distance of the oil immersion microscope objective in the trapping setup. Thinner PDMS layer can be made by simply increasing the spin speed in the spin-coating step.

In another example, a double-nanohole in a gold film is integrated in a microfluidic channel or flow cell that is made from PDMS, glass, plastic, or other materials. For example, a PDMS microfluidic flow-cell can be configured to conduct flow to a double nanohole in a gold layer. The PDS flow-cell can be defined with one or more PDMS layers that are supported by a glass substrate such as a cover slip. Zehtabi-Oskuie et al., "Flow-dependent double-nanohole optical trapping of 20 nm polystyrene nanospheres," Scientific Reports, 2, 966 (2012), which is incorporated herein by reference describes one such PDMS-based flow cell.

Figures 10A, 10B, 10C, 10D, 10E, 10F, 10G:
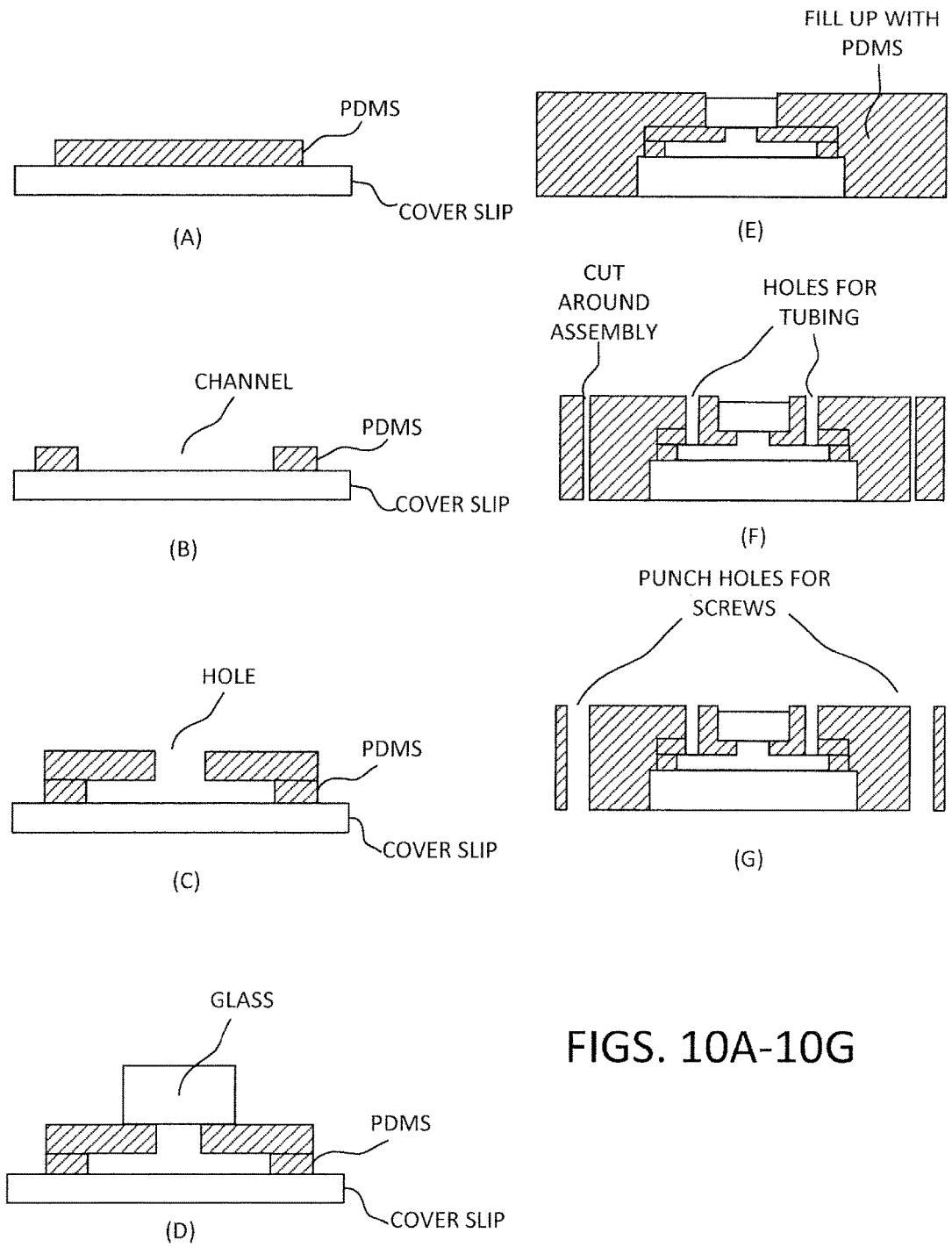
FIGS. 10A-10I illustrate fabrication of a flow channel that includes a double nanohole trap.
Figure 10H:
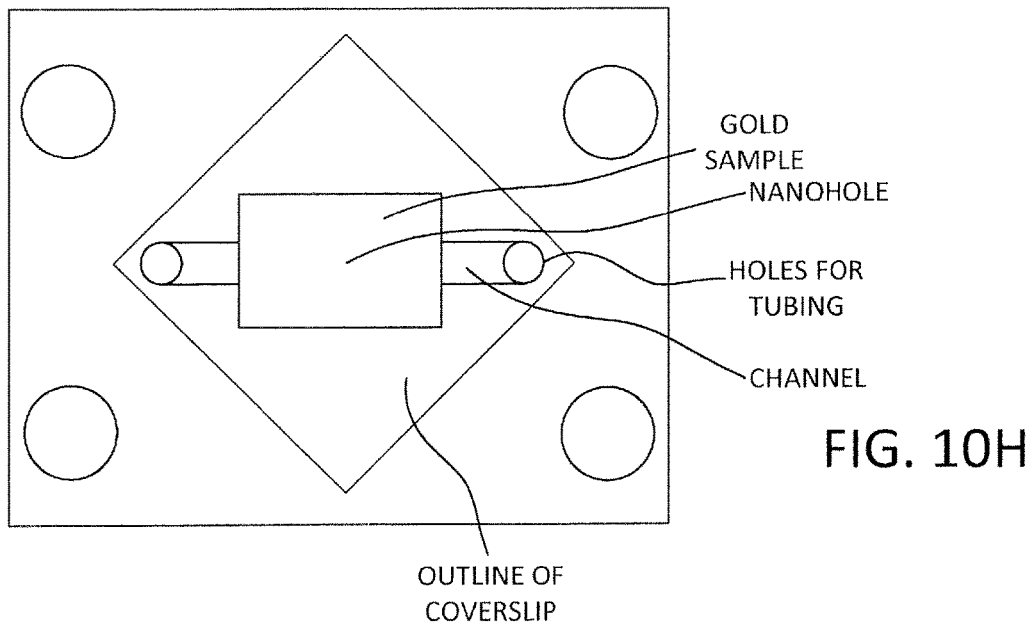
Figure 10I:
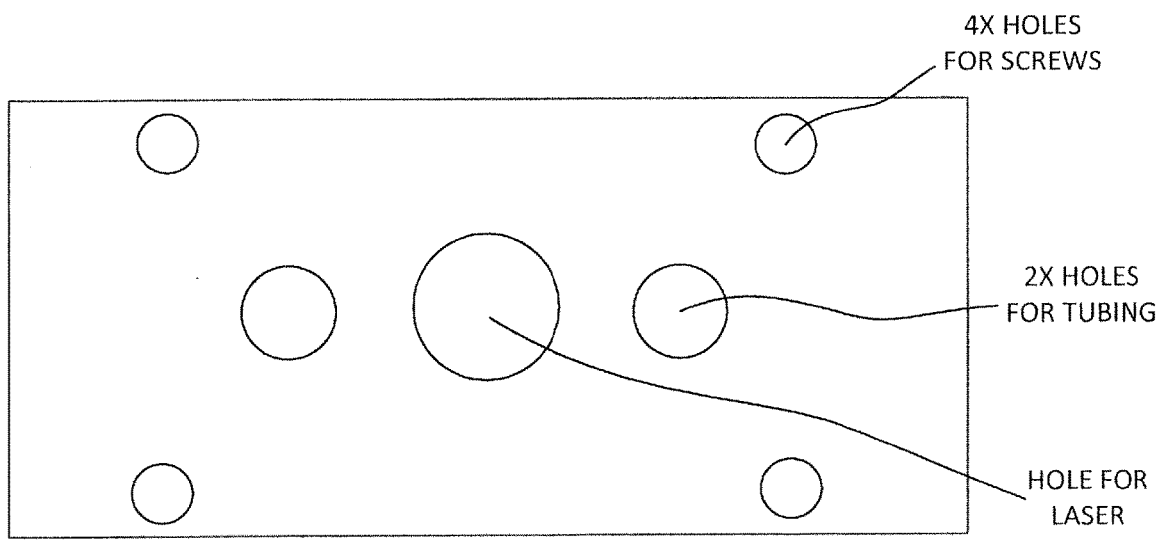
Figures 11A, 11B, 11C, 11D, 11E, 11F:
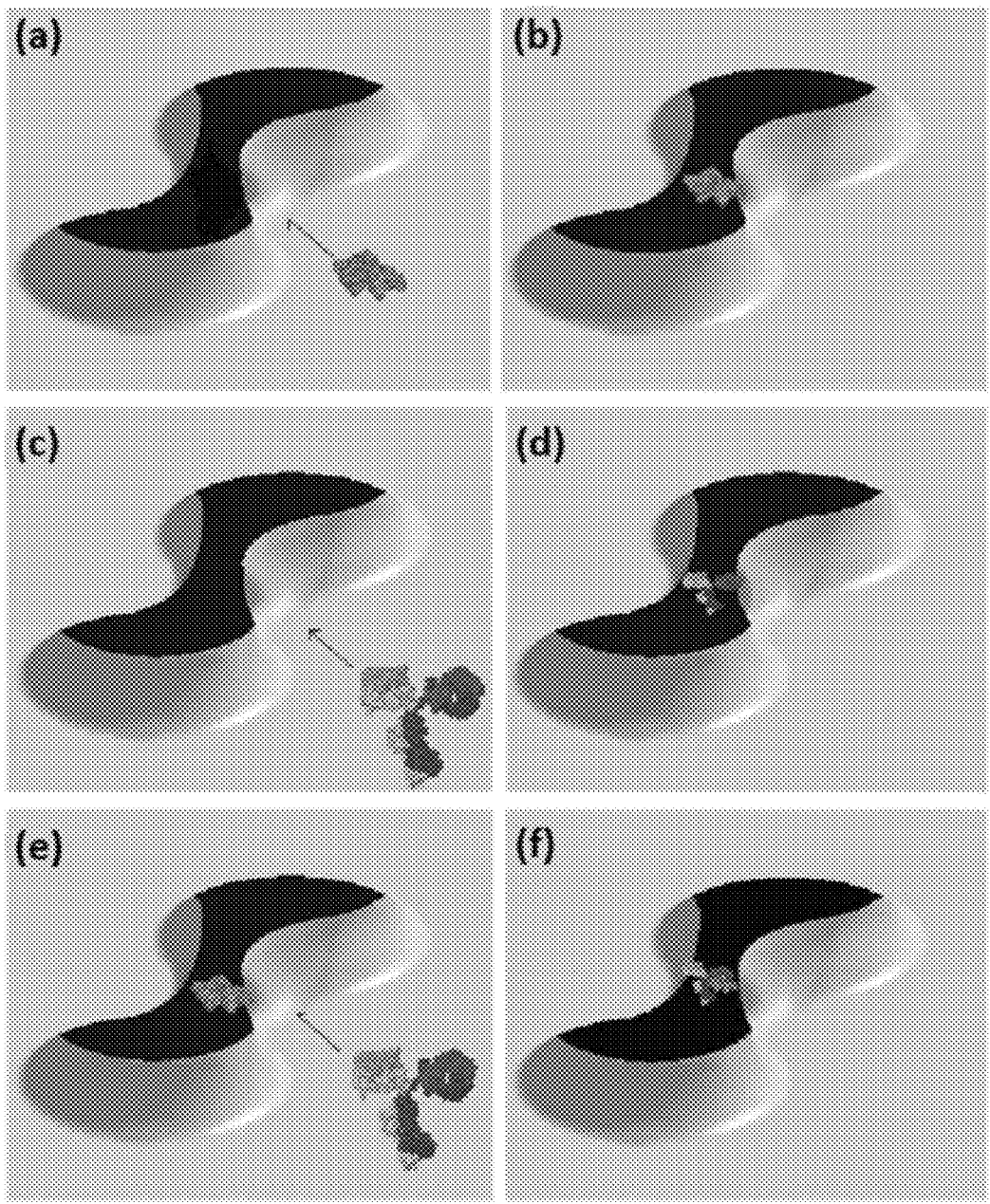
FIG. 11A illustrates the approach of a single BSA particle to a double nanohole.
FIG. 11B shows a single BSA particle trapped between tips of the double nanohole.
FIG. 11C shows an anti-BSA particle approaching the vacant trap.
FIG. 11D shows an anti-BSA particle trapped between the tips of the double nanohole.
FIG. 11E shows an anti-BSA particle introduced into a system with a BSA particle already trapped.
FIG. 11F shows an anti-BSA and a BSA particle co-trapped between the cusps of the double-nanohole.

Referring to FIGS. 10A-10G, a microfluidic flow cell with a double nanohole can be formed by pouring PDMS in the petri-dish and spin coating to create a thin layer and then putting a glass cover slip on top of the PDMS. The assembly is then baked at 75 Celsius to harden the PDMS (FIG. 10A). The cover slip and the PDMS under it are cut out. Then the channel is cut out diagonally on the cover slip (FIG. 10B). Another layer of PDMS is prepared in a separate petri-dish and a piece with the same size as the cover slip is cut out of it. A hole is cut out at the centre and it is placed on the top of the channel on the cover slip (FIG. 10C). Then the gold film in which the double-nanohole has been fabricated is placed on top of this hole (FIG. 10D). The whole configuration is then placed in another petri-dish and PDMS is added into it so that it covers all of these parts (FIG. 10E). In this step the PDMS will penetrate below the cover slip and lift it a little. Next, the PDMS is baked, and two holes are punched for tubing (FIG. 10F). Four holes are punched for screws which hold the whole configuration on an aluminum clamp (FIG. 10G). Wiring is used in order to support the tubes so that tube fittings are not affected by any movement. FIGS. 10H-10I show the configuration view from the top.

Figure 7A:
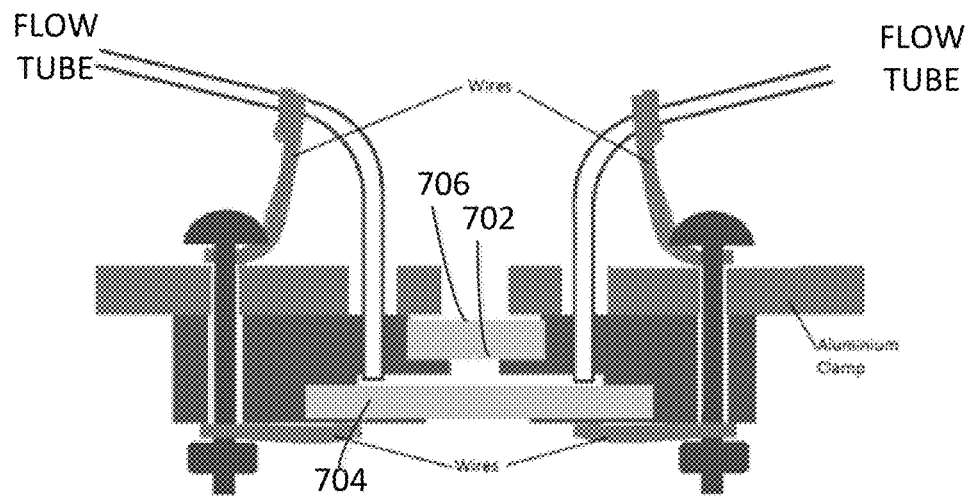
FIGS. 7A-7B are sectional views of a flow cell configured to include a double nanohole trap and used to demonstrate trapping in the presence of flow.
Figure 8:
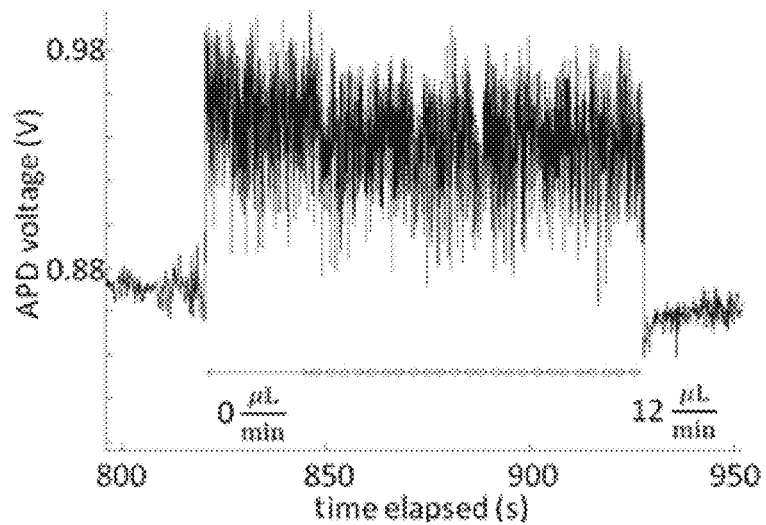
FIG. 8 is a graph of transmitted optical power as a function of fluid flow rate, wherein flow rate is increasing as a function of time.
Figure 7B:
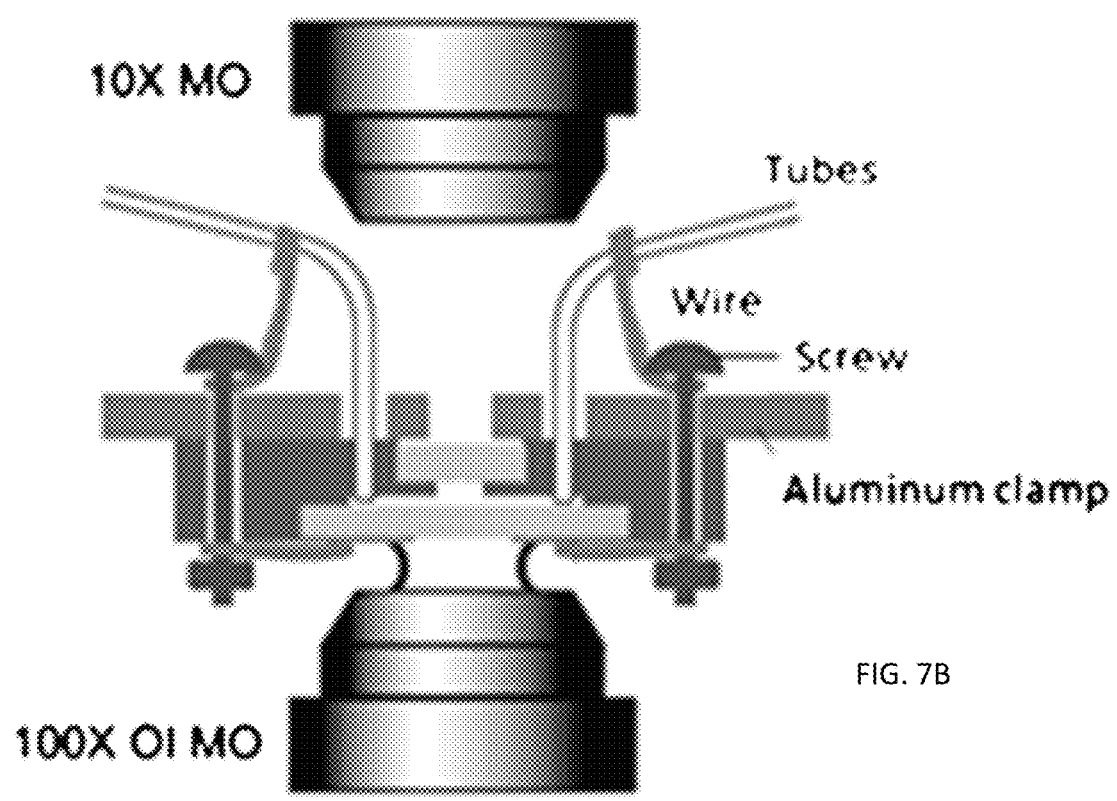

A complete assembly is shown in FIGS. 7A-7B. PMS layers 704, 706 defined a cavity 708, and a gold layer 702 in which a double nanohole is formed is secured to the PDMS laser 706. Flow tubes for introduction of materials into the cavity 708 are also shown, along with a claim that secures the assembly. Other configurations are possible, and this is a convenient example.

Figure 2:
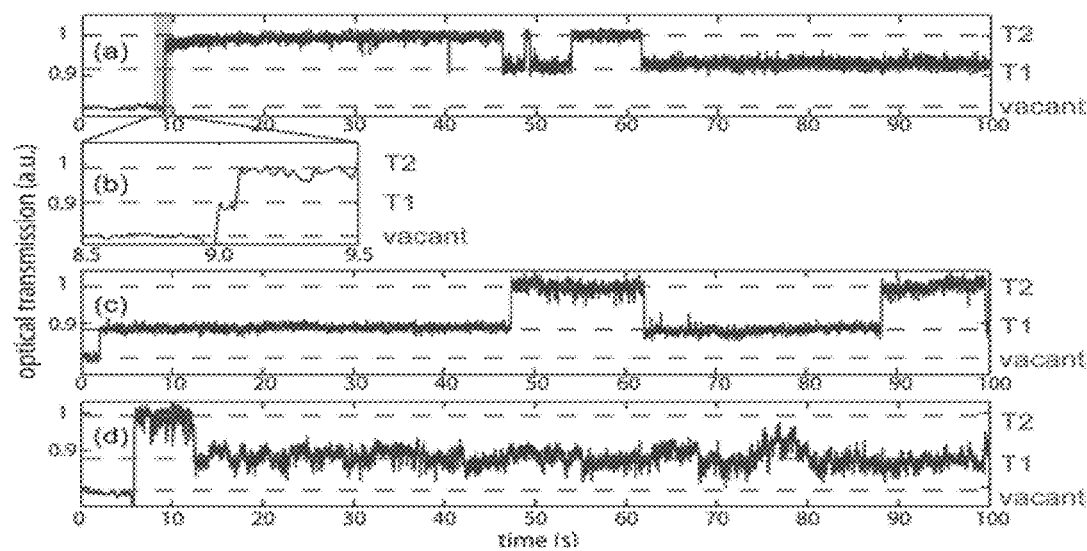
FIG. 2 includes graphs of transmitted optical power through the double-nanohole as a function of time using a BSA solution in PBS buffer with pH=7.4 at various incident optical powers. Inset (a) is at a power of 13.4 mW, inset (b) is an enlarged view of a portion of (a), insets (c)-(d) are at incident optical powers of 10.6 mW and 8.5 mW, respectively. An untrapped (vacant) state and two trapped states (T1 and T2) are clearly shown.

FIG. 2 shows time traces of transmitted power through the double-nanohole. When a protein molecule with a greater refractive index than that of water comes between the tips of the double-nanohole, it dielectrically loads the region with the most intense local field enhancement, thereby significantly increasing the light transmission. By Newton's third law, the change of light momentum reacts on the molecule, forming an optical force, which favors trapping. The distinct jumps in the light transmission serve also as a convenient and highly-sensitive sensor for the individual molecules with a signal-to-noise ratio (SNR) of at least 33. The type of trapping seen in FIG. 2 was found consistently for all trapping events observed and for measurements on different days over a lengthy period.

Figure 3:
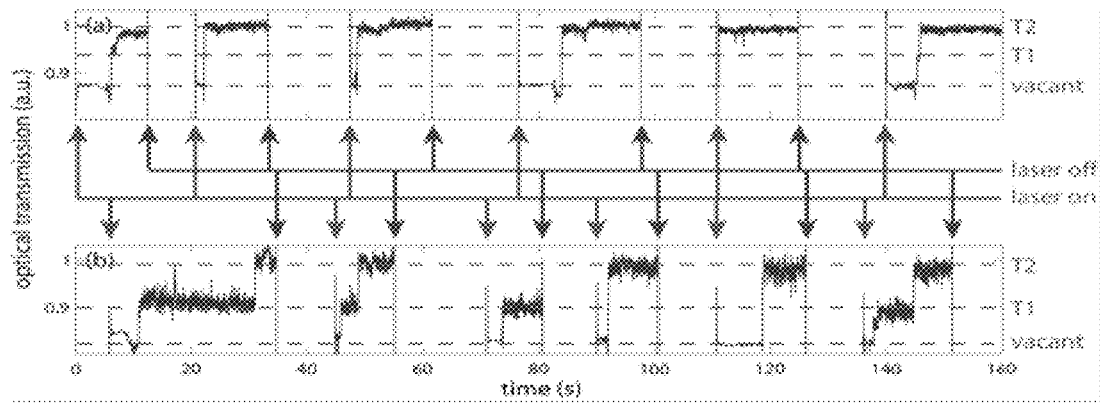
FIG. 3 includes graphs of transmitted optical power through the double-nanohole as a function of time, showing reversibility of trapping by turning the laser on and off, using incident optical powers of (a) 13.4 mW and (b) 5.3 mW, respectively.

FIG. 3 shows the reversibility of trapping, which demonstrates that the optical force is the underlying mechanism in trapping. To block the protein molecule from adsorbing to the Au surface, a monolayer of mPEG thiol was formed on the Au surface before the trapping experiment. This was done by immersing the Au film sample in a 5 mM aqueous solution of mPEG thiol (with a molecular weight of 5000) at room temperature overnight, and rinsing thoroughly with deionized water to remove any nonchemical absorbed mPEG thiol molecules. Those skilled in the art will understand there are other methods for creating the same effect on other metal surfaces. The release of the protein was observed after it had been trapped. To do this, the trapping laser beam was turned off after a trapping event, and then turned back on after approximately 10 s. As FIG. 3 shows, the transmitted power falls back to the "vacant" state each time the trapping laser is reapplied after being turned off, and jumps back to the trapping states after a certain amount of time showing re-trapping. This result clearly shows that the trapped protein molecule is released when the trapping laser beam is turned off. In experiments using the same setup but with a longer laser wavelength, silica spheres that do not have a tendency to adsorb to gold were capable of being trapped.

An interesting feature of the protein trapping experiment is the ubiquitous appearance of two discrete levels of the trapping state. Two hypotheses can be considered to explain this "double-step". First, a single molecule and a two-molecule dimer might be trapped in the lower (T1) and the higher (T2) trapped states, giving different dielectric loading area and therefore different transmission change. However, that hypothesis is deficient in explaining that the double-step appeared in every instance of trapping, and furthermore, it was never observed in polystyrene and silica nanosphere studies.

A more likely hypothesis is that the protein molecule is actually unfolded after being trapped. Unfolding between the N and F forms of the protein molecule has been observed by changes in pH. The optical polarizability increases with the elongated F form of the protein molecule under consideration, hence a stronger trapping potential is formed and more light is transmitted. In other words, the trap is strong enough to actually unfold the protein, since the trap already overcomes the Brownian motion of the protein for timescales of the order of minutes. FIGS. 2(b)-2(c) show that for lower powers, the particle spends less time in the unfolded state. This supports the hypothesis that the trap actually unfolds the protein because the optical force is weaker for lower powers. FIG. 3 also shows similar dependence of the unfolding tendency on the trapping power at the instance when the trapping beam is turned on.

In addition to the dependence on the incident power, the step between the two trapped states corresponds to an optical force in aperture trapping through Newton's third law, as described above. Since the step to trap folded a protein molecule is comparable to the step to unfold, it stands to reason that the energies associated with each of these events are comparable, and therefore of the order of the energy associated with thermal motion itself.

There is expected to be a smaller contribution to the ability to unfold the protein that arises due to increased local temperatures at higher powers. The percentage power changes are much larger than the absolute temperature changes, and so this effect is expected to be negligible. If the temperature change was noticeable, a comparable reduction in the trapping time and increased fluctuations due to Brownian motion for increased laser power would be observed; however, trapping time reduction was not observed and an opposite dependence of fluctuation on laser power was observed. The working temperature at the trapping point is clearly below the critical operating temperature which is the denaturing temperature of the particular protein molecule. If the temperature was higher, the protein would irreversibly unfold, and reversible unfolding would not be observed as FIG. 2 shows. Under this small temperature change, it is more likely that thermal effects have negligible contribution to the trapping and unfolding of protein.

Figure 4:
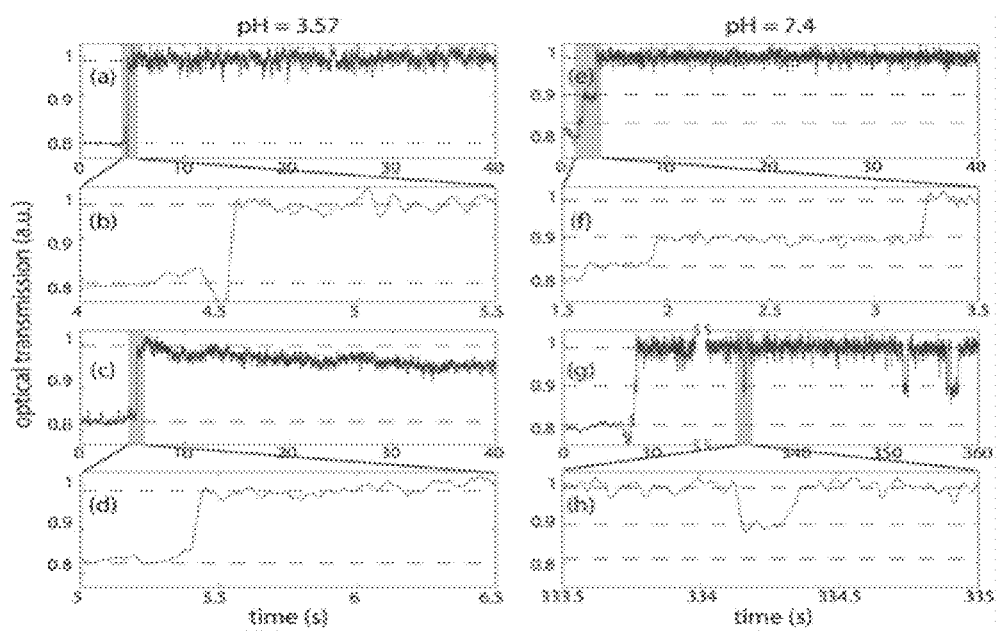
FIG. 4 includes graphs of transmitted optical power through the double-nanohole as a function of time using an incident optical power of 8.4 mW in a BSA solution in PBS buffer with pH=3.57 ((a)-(d)), and pH=7.4 ((e)-FIG. (h)).

To further test the protein-unfolding hypothesis, the trapping experiment in a solution was repeated with a lower pH of 3.57. Under such a pH, the protein molecule is already in the F form. FIG. 4 compares the time traces of transmitted optical powers under pH=3.57 and pH=7.4 environments, using the same incident laser power of 8.4 mW. As expected, the double-step only appears in the higher-pH environment; it does not appear in the lower-pH but otherwise identical environment, neither at the transition when the trapping initially starts nor in the trapped state. This result confirms that the double-step in the transmission power comes from transitions between two forms of the protein molecule.

Fluctuations in the optical transmission once the particle is trapped are predominantly the result of Brownian motion, not noise from the detection system. The noise from the detection system can be observed before the trapping event and it is significantly lower (at least by a factor of 5). Spectral analysis of the intensity fluctuations were found to be at lower frequency 3-dB shoulder for the unfolded protein than the folded protein, which may be attributed to the increased drag associated with the unfolded state for motion along the z-axis, with molecules long axis along the x-direction. Since the trapping minimum is at the surface, this is clearly not a harmonic potential. Furthermore, there are hydrodynamic interactions with the surfaces of the aperture.

In addition to monitoring folding events in proteins, or other molecules, a double-nanohole trap can be used to monitor interactions between particles (such as binding) at the single molecule level. For example, co-trapping of a protein (BSA) with its anti-body (anti-BSA) can be accomplished. In one example, a dual syringe pump is situated to for sequential delivery of a protein and its antibody. FIGS. 11A-11F show a schematic of a protein/antibody trapping cotrapping experiment, where a, b, c, d, e, f show flowing in of ultra-pure BSA (AM2616, Life Technologies), trapping of BSA, flowing in polyclonal anti-BSA (A11133, Life Technologies), trapping of anti-BSA, flowing in of anti-BSA while BSA is trapped, and co-trapping of BSA with anti-BSA. A thiolated PEG layer was attached to the gold film to help prevent adhesion of the proteins. Concentrations used were 0.1% w/v for the BSA in phosphate buffer saline solution.

Figure 12:
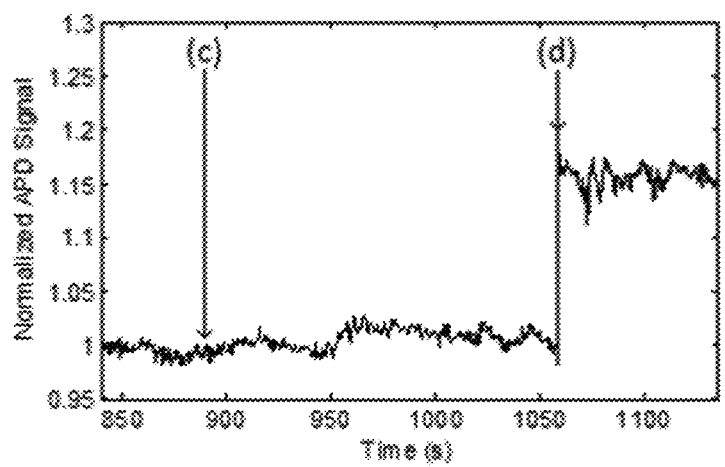
FIG. 12 illustrates a typical trapping signal of an anti-BSA particle. The letters (c) and (d) are as indicated in FIGS. 11A-11F.

FIG. 12 shows the trapping of anti-BSA as seen by a jump in the transmission through the aperture measured with an APD. While the step-size depends on the aperture used, it was found that the step-size for trapping anti-BSA alone was typically about 2 times larger than BSA alone, which is reasonable since anti-BSA is three times larger than BSA. There is typically no direct correlation between the particle size and the trapping signal because of the different shapes of the BSA and anti-BSA particles; however, the expected trend is that larger particles will show a larger signal.

Figure 13:
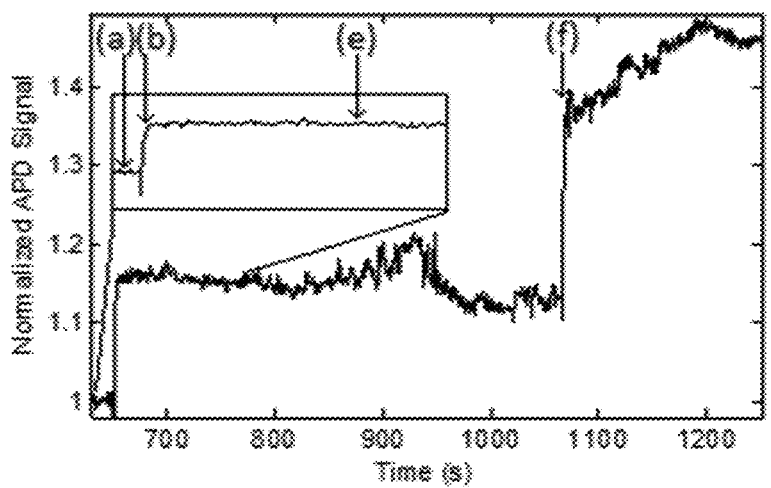
FIG. 13 illustrates co-trapping of BSA with anti-BSA. After flowing in BSA (a), BSA trapping occurs (b), followed by flowing in anti-BSA (e), and anti-BSA co-trapping (f). The letters (a), (b), (e) and (f) refer to the schematic of FIGS. 11A-11F.

FIG. 13 shows the trapping and subsequent co-trapping of BSA and anti-BSA, where the anti-BSA is flowed into the microchannel once trapping of BSA is achieved. BSA was generally not released from the trap when a moderate flow rate of 5 ml/min was used.

Figure 14:
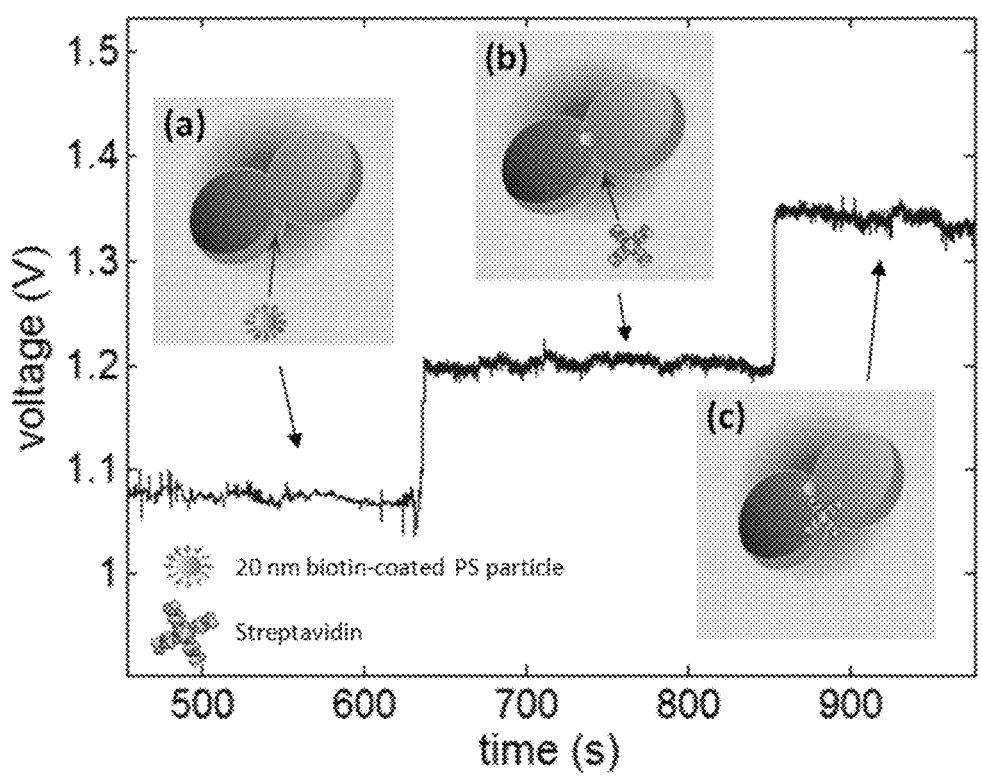
FIG. 14 illustrates signals associated with co-trapping.

In other examples, binding between streptavidin and biotin-coated nanospheres can be detected. This is shown in FIG. 14 where initially a 20 nm biotin-coated particle is trapped in a double-nanohole optical trap. Then streptavidin is flowed in and a second step in the optical transmission confirms that streptavidin is trapped as well. Subsequent measurements confirm that biotin-streptavidin binding is playing a role in the co-trapping here, since if the initial 20 nm particle has no biotin, or if the streptavidin is saturated with biotin bonds prior to being introduced into the trapping environment, no co-trapping is observed. Referring to FIG. 14, inset (a) shows inflow of biotin-coated polystyrene nanoparticles, associated with a signal jump at ~630 s corresponding to trapping of one of these nanoparticles, inset (b) shows inflow of streptavidin at around 780 s, associated with a signal jump at around 850 s corresponding to trapping of streptavidin as well, as shown in inset (c).

The SNR of the disclosed system can be high. Therefore, a double-nanohole is very sensitive, and can be used as a biosensor for single molecule detection. Sensing and trapping are often the "dual-functionality" of one optical system. For example, whispering gallery mode (WGM) optical micro-resonators are common setups for both sensing and trapping. Compared to an optical micro-resonator, the double-nanohole does not rely on a high-quality resonance and simply measuring the transmitted power can perform the sensing.

Figure 15:
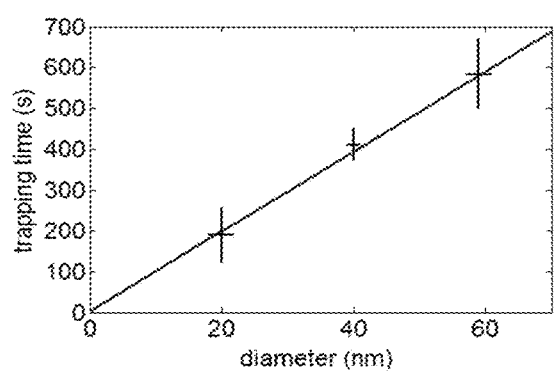
FIG. 15 illustrates trapping time as a function of particle diameter for polystyrene particles.
Figure 16:
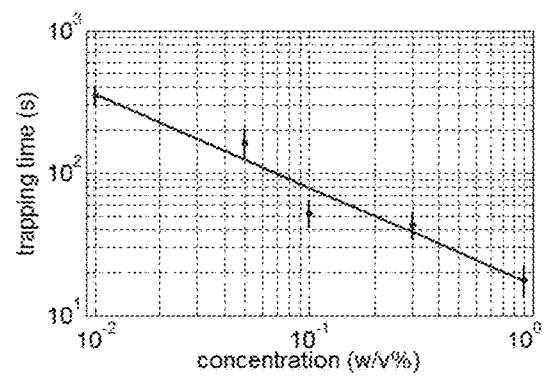
FIG. 16 illustrates trapping time as a function of polystyrene particle concentration.

For sensing applications, the size and/or concentration of particles in solution can be estimated by monitoring the average time to trap through diffusion. FIGS. 15-16 show dependent of trapping time by diffusion for of polystyrene particles as a function of particle diameter and concentration, respectively. FIGS. 15-16 illustrate measurement accuracy of about 1 nm (particle size) and an order of magnitude (concentration), but measurements of superior accuracy can be obtained. In some examples, a detection system can be provided with a signal processing system configured to provide particle size or particle concentration estimates.

Figure 17:
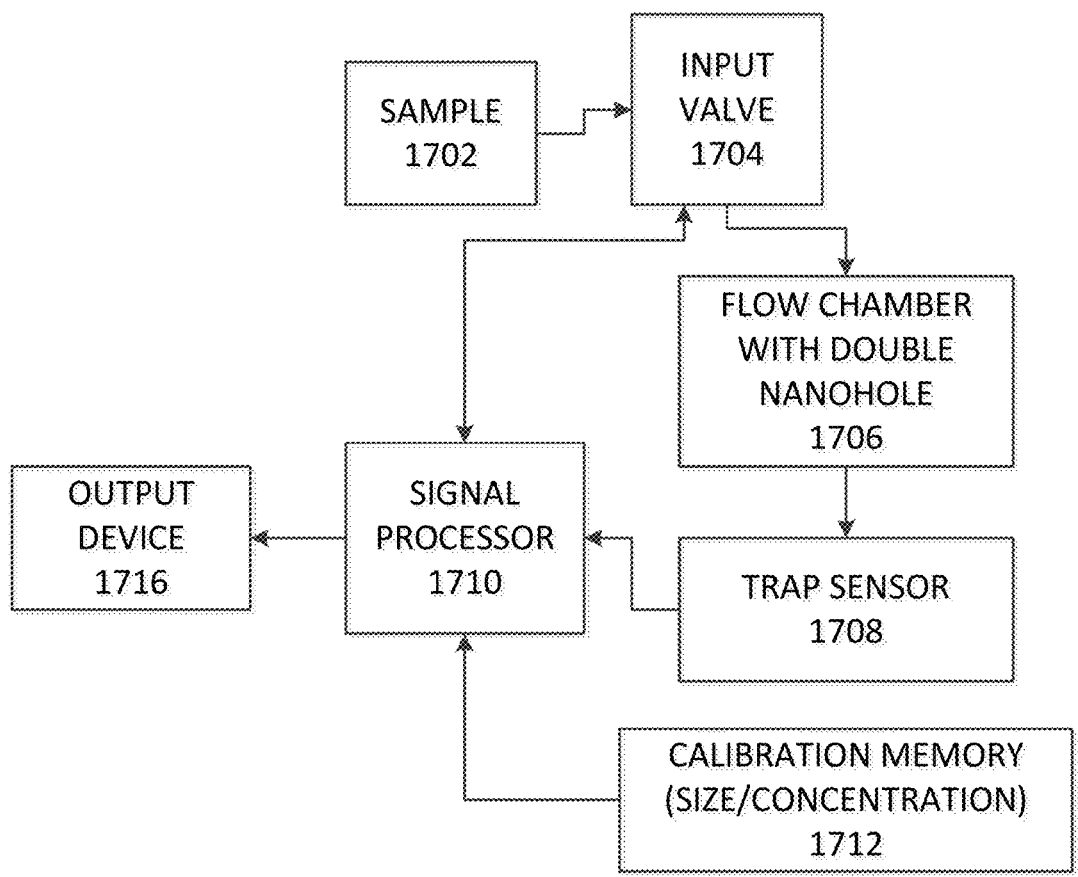
FIG. 17 illustrates a sensor system for measuring particle size or concentration as a function of trapping time.

FIG. 17 illustrates a representative system configured to provide estimates of particle size and/or concentration. A sample chamber 1702 is coupled to an input valve 1704 that is configured to direct a sample volume to a flow chamber with a double nanohole 1706. A trap sensor (such as an optical sensing system) is configured to provide a signal associated with particle trapping and is coupled to a signal processor 1710. Based on a time at which the input value 1704 admitted the sample to the flow chamber, the signal processor 1710 determines an estimate of particle size or concentration. In some cases, the signal processor 1710 is coupled to memory 1712 that stores calibration information for size or concentration estimates. The signal process 1710 couples the size or concentration estimate to an output device 1716 such as a viewable display, or the estimate can be communication as a digital or other numerical value for additional processing or recording keeping.

Selectivity in detection can be provided based on detection of fluorescence emitted from the trapped molecule, and, in some cases, the trapping laser source can be used to stimulate fluorescence as well. Raman spectra can be obtained from the trapped molecule as well, and the trapping laser can be used in some cases as the pump source. A specific binding molecule can be directed to the trapped molecule for tagging the trapped molecule, to provide additional modulation of transmitted optical power. In other examples, a trapped particle can be moved in the trap to a different location where it can be isolated and analyzed by different methods, such as electron microscopy or mass spectroscopy.

Figure 9A:
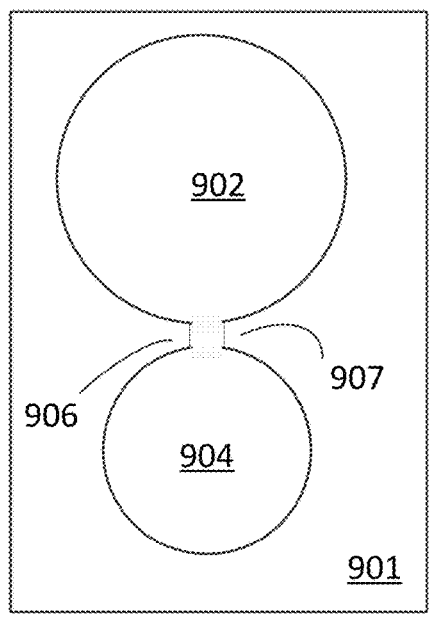
FIGS. 9A-9C illustrate a few alternative configurations.
Figure 9B:
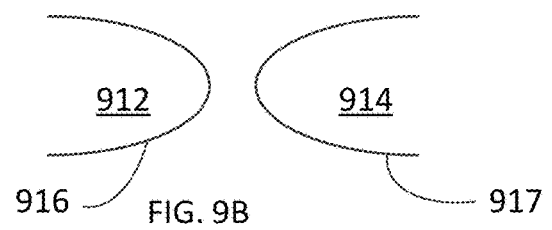
Figure 9C:
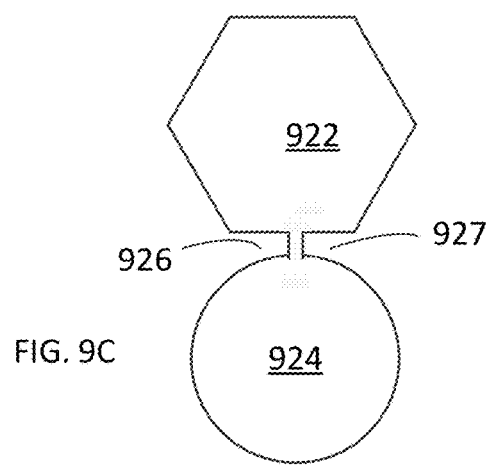

In the examples above, two equal radius circular nanoholes are used to define cusps or tips in a conductive sheet that can be used in trapping. Typically, holes of any shape or combination of shapes can be used, and the holes are preferably situated within a few nm or few tens of nm of each other. For example, FIG. 9A illustrates a trapping assembly that includes circular apertures 902, 904 defined in a conductive substrate 901. The apertures 902, 904 have different diameters and are situated close together so as to define tips or cusps 906, 907. In another example shown in FIG. 9B, portions of ellipses or other curves 916, 917 define tips 912, 914. In yet another example shown in FIG. 9C, a circular aperture 924 and a hexagonal aperture 922 define tips 926, 927. In other examples, circles, ellipses, arcs, regular or irregular polygons, or other shapes and combinations of shapes can be used. Different shapes of different sizes can be used, or similar shapes with similar sizes can be used. Shapes can be characterized as having effective radii that correspond to a circular shape of the same area. Typically, effective radii $R_{eff}$ are less than about 500 nm, 400 nm, 250 nm, or 100 nm, and the shapes are situated within about 1, 0.7, 0.5, or 0.2 $R_{eff}$ so as to define tips or cusps. A ratio of shape dimensions along a long direction and a short direction is generally less than about 20, 10, 5, or 2. For large values of this ratio, shapes can be spaced apart by about $1/20$, $1/10$, $1/5$, or $1/2$ $R_{eff}$ so as to define cusps.

In view of the many possible embodiments to which the disclosed technology may be applied, it should be recognized that the illustrated embodiments are only examples of the disclosed technology and should not be taken as limiting the scope of the disclosure.

We claim:
1. A sensor, comprising:
   an optical trap including an aperture defining a pair of cusps; and
   an optical system configured to provide an indication of an optical trapping by the optical trap based on optical power received from the optical trap.
2. The sensor of claim 1, wherein the optical system is configured to provide the indication based on a variation in optical transmittance associated with trapping.
3. The sensor of claim 1, wherein the indication of the optical trapping is associated with a trapped particle size, a concentration of trapped particles, or both.
4. The sensor of claim 1, wherein the optical system is configured to provide an indication of at least two trapping states.

5. The sensor of claim 1, further comprising a chamber configured to receive a sample, wherein the optical trap is coupled to the chamber so as to be exposed to the received sample.

6. The sensor of claim 5, wherein the pair of cusps are defined by a double-nanohole.

7. The sensor of claim 6, wherein the double-nanohole is defined in a conductive layer that is situated to be exposed to an interior of the chamber.

8. The sensor of claim 5, wherein the chamber is a flow through chamber.

9. The sensor of claim 1, wherein the pair of cusps is defined in a conductive layer by opposing apertures.

10. The sensor of claim 9, wherein the apertures are circular, arcuate, or elliptical.

11. A method for optically trapping a portion of a sample, comprising:
    applying the sample to a plasmonic tip pair defined by the pair of cusps of the optical trap of claim 1, the plasmonic tip pair having a predetermined tip gap; and
    exposing the sample and the plasmonic tip pair to optical radiation polarized parallel to an axis extending between the tip pair so as to optically trap at least a portion of the sample.

12. A sensor, comprising:
    an optical trap that includes a pair of cusps defined in a conductive layer; and
    an optical system configured to provide an indication of an optical trapping by the optical trap based on optical power received from the optical trap.

13. A sensor, comprising:
    an optical trap including a double nanohole assembly; and
    an optical system configured to provide an indication of an optical trapping by the optical trap based on optical power received from the optical trap.

14. The sensor of claim 13, wherein the optical system includes an optical radiation source configured to irradiate the nanohole assembly.

15. The sensor of claim 14, wherein the optical system includes an optical radiation detector configured to provide the indication of trapping based on detected optical power.

16. The sensor of claim 14, wherein the double nanohole assembly defines a first conductive tip and a second conductive tip having a tip separation in the range of about 10 nm to about 500 nm.

17. The sensor of claim 16, wherein the optical system includes a waveplate configured to provide a state of polarization of the optical radiation from the optical radiation source that is aligned with a gap between the first and second conductive tips.

18. The sensor of claim 16, wherein the double nanohole assembly includes two nanoholes defined in a plasmonic layer, and the tips are defined by the two nanoholes in the plasmonic layer.

19. The sensor of claim 18, wherein the plasmonic layer is a metal or doped dielectric layer.

20. A method of producing a trapping state at an optical trap, comprising:
    receiving a specimen at the double nanohole assembly of the optical trap of claim 13; and
    applying optical radiation to the optical trap so as to produce the trapping state at the double nanohole assembly.

21. The method of claim 20, wherein, based on optical radiation transmitted by the optical trap, identifying the trapping state.

22. The method of claim 20, further comprising providing a reagent selected so as to modify a property of the specimen at the double cusp assembly.

23. The method of claim 21, further comprising identifying at least two trapping states based on the transmitted optical radiation.

24. The method of claim 21, wherein the double nanohole assembly is defined in a conductive layer by opposing apertures.

25. The method of claim 24, wherein the apertures are triangular, rectangular, polygonal, circular, arcuate, or elliptical.

26. The method of claim 25, wherein the apertures have different sizes or shapes.

27. A method for translating an optically trapped particle, comprising:
    optically trapping a particle at the double nanohole assembly of the optical trap of claim 13; and
    translating the double nanohole assembly with the optically trapped particle.

28. The method of claim 27, further comprising forming a combined product with the translated trapped particle and one or more binding molecules.

29. The method of claim 27, further comprising monitoring the translated trapped particle.

30. The method of claim 27, wherein the double nanohole assembly is situated proximate an optical fiber, and further comprising detecting a characteristic of the trapped particle based on optical radiation coupled into the optical fiber.

* * * * *